(12) United States Patent
Pedicini et al.

(10) Patent No.: US 12,245,800 B2
(45) Date of Patent: *Mar. 11, 2025

(54) ROTARY IMPACTOR FOR ORTHOPEDIC SURGERY

(71) Applicants: Christopher Pedicini, Brentwood, TN (US); Joshua Pedicini, Nashville, TN (US)

(72) Inventors: Christopher Pedicini, Brentwood, TN (US); Joshua Pedicini, Nashville, TN (US)

(73) Assignee: FIDELIS PARTNERS, LLC, Cheyenne, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/518,076

(22) Filed: Nov. 22, 2023

(65) Prior Publication Data
US 2024/0085709 A1 Mar. 14, 2024

Related U.S. Application Data

(63) Continuation of application No. 17/584,349, filed on Jan. 25, 2022, now Pat. No. 11,877,780.

(60) Provisional application No. 63/277,754, filed on Nov. 10, 2021, provisional application No. 63/188,542, filed on May 14, 2021, provisional application No. 63/141,786, filed on Jan. 26, 2021.

(51) Int. Cl.
| | |
|---|---|
| *A61B 17/92* | (2006.01) |
| *G02B 27/01* | (2006.01) |
| *G06F 3/00* | (2006.01) |
| *G06F 3/01* | (2006.01) |

(52) U.S. Cl.
CPC .......... *A61B 17/92* (2013.01); *G02B 27/0172* (2013.01); *G06F 3/005* (2013.01); *G06F 3/017* (2013.01); *G02B 2027/0138* (2013.01); *G02B 2027/0187* (2013.01)

(58) Field of Classification Search
CPC ....................................... A61B 17/92
See application file for complete search history.

(56) References Cited

U.S. PATENT DOCUMENTS

| | | | |
|---|---|---|---|
| 7,402,040 B2 | 7/2008 | Turri | |
| 2008/0210451 A1* | 9/2008 | Aoki | B25D 17/24 173/162.1 |
| 2010/0268235 A1 | 10/2010 | Teichmann | |

(Continued)

OTHER PUBLICATIONS

Extended European Search Report issued Dec. 2, 2024 in corresponding European Patent Application No. 22746488.0, 11 pages.

*Primary Examiner* — Christian A Sevilla
(74) *Attorney, Agent, or Firm* — XSENSUS LLP

(57) ABSTRACT

A rotary impactor for orthopedic surgery includes an output anvil and a hammer that is capable of imparting linear and rotary force on the anvil. The anvil may be moveable on a leadscrew element to alternately generate energy in an energy storage means and to move along the leadscrew element to impact the anvil. A viscoelastic mechanism or a dampening mechanism is used to reduce the reflected force and or torque during operation of the rotary impactor. High frequency linear impacts by the impactor obviate the need for a surgeon to provide an external push force on the impactor in order to perform a successful surgical operation.

20 Claims, 13 Drawing Sheets

(56) References Cited

U.S. PATENT DOCUMENTS

| | | | |
|---|---|---|---|
| 2012/0232562 A1* | 9/2012 | Mani | A61F 2/4612 606/100 |
| 2015/0182351 A1* | 7/2015 | Behzadi | A61B 17/92 606/91 |
| 2018/0055552 A1* | 3/2018 | Pedicini | A61B 17/92 |
| 2019/0216521 A1* | 7/2019 | Chhatrala | A61B 17/921 |

* cited by examiner

ROTARY IMPACTOR FOR ORTHOPEDIC SURGERY

CROSS-REFERENCE TO RELATED APPLICATIONS

The present application is a non-provisional application and is a continuation under 35 U.S.C. § 111 of U.S. Non-Provisional patent application Ser. No. 17/584,349 filed on Jan. 25, 2022, and under 35 U.S.C. § 119 on U.S. Provisional Patent Application Ser. No. 63/141,786, filed on Jan. 26, 2021, on U.S. Provisional Patent Application Ser. No. 63/188,542, filed on May 14, 2021, and on U.S. Provisional Patent Application Ser. No. 63/277,754, filed on Nov. 10, 2021, the disclosures of which are incorporated by reference.

FIELD OF THE DISCLOSURE

The present disclosure relates to a rotary impact reamer for use by surgeons and or surgical robots, and more particularly, to a rotary impact reamer in which negligible reactionary force is imparted to the surgeon and/or robot.

BACKGROUND OF THE DISCLOSURE

The current direction of surgery is towards using robot assistance in the surgery process. In this regard, an end effector of the robot may be used by a robot, for example, to perform a surgical procedure. The end effector is, in an embodiment, a device, tool, or manipulator at an end of the robot that is capable of engaging and interacting with a surgical site. The end effector is directed by the robot to perform surgical actions. In the field of robotic surgery, the end effector may comprise a surgical tool.

To date, robotic automation in surgery has worked well in laproscopic procedures and surgeries with low energy requirements, however, in the orthopedic environment where large forces and energies are routine, the adoption of the robot has been hindered. In such an environment and in the field of orthopedic surgery, larger energy requirements have necessitated a different approach (such as machining) due to the inability of surgical robots to handle the magnitude of reactionary forces that result from typical large bone surgical tools (such as saws, drills or reamers).

An exemplary robot that is used in large bone surgeries is Stryker Corporation's MAKO product. The MAKO has three purposes: enhanced planning, dynamic joint balancing, and robotic-arm assisted bone preparation.

As part of its operation, the robot must have the bone geometry of the surgical site identified in order to accurately navigate, guide, and manipulate its end effector through the surgical site. Such identification of bone geometry is referred to as registration. Existing surgical power tools produce a significant amount of reactionary torque (such as in the case of a surgical reamer) or shock (such as in the case of a surgical impacting tool) when used in orthopedic surgery. This torque and or shock can not only cause the robot to lose its registration but it can also damage the robot's highly intricate machinery and components.

Rotary reamers are used in hip and hip replacement surgery such as when preparing the cavity for the acetabular cup of a prosthetic hip. These rotary tools have a significant reactionary torque associated with the surgical procedure. This can result in the tool being wrenched from the grip of the surgeon performing the operation and in severe cases damage to the surgeons wrist or forearm. Clearly, such reactionary torque can cause navigational or guidance errors which in the case of use by a robot will often result in loss of registration and shut down of the robot. Testing has shown this to be the case and is one of the most common complaints about using robots for large bone orthopedic surgery.

The navigation capability is arguably the most important feature of orthopedic robotics. For a successful surgery, the robot must hold the tool (or instrument) in the correct orientation and alignment with respect to the bone. If the surgical instrument is allowed to move off the stereotactic boundary then the surgery can suffer from any of a number of drawbacks, including injury to soft tissue if the instrument is still powered. Currently-available rotary tools can generate large destabilizing forces (reactionary torque caused by the reamer encountering and/or snagging on a hard section of bone). These forces interfere with a robots programmed navigation and can result in the robot shutting down.

Furthermore, there are at least two problems with simply placing a surgical power tool designed for a surgeon onto a robot. One, the reactionary force/torque imparted by the tool can move the robot off of its guided path. Secondly in large bone surgery, the robot often cannot supply sufficient linear force to enable progression of the reamer into the acetabulum. The surgeon often has to exert linear force on the tool in order to achieve the desired outcome.

Accordingly, a need exists for an impacting tool (also referred to herein as an impactor) that allows for easier operation by the surgeon as well as creating a pathway to robotic and eventually full autonomous surgery. As such, the present disclosure provides for a rotary and or rotary/linear surgical tool which through the use of impacting significantly reduces the reflected torque while achieving a similar outcome as current rotary surgical reamers. Furthermore in the case that linear impaction is used to augment the rotary impaction, both the linear and rotary force requirements are significantly reduced as compared to conventional surgical reamers and drills. For example, current art requires the surgeon to apply all the required linear force to advance the surgical reamer into the surgical site. This linear force can be in excess of 25 pounds, which is far more than a surgical robot is capable of providing. It has been discovered that linear impaction by the disclosed tool reduces the required linear supporting force from the surgeon by ~50%.

SUMMARY OF THE DISCLOSURE

In view of the foregoing disadvantages inherent in the prior art, the purpose of the present disclosure is to provide a solution to the high reactionary forces that occur from the use of orthopedic surgical tools. These solutions work to reduce the reactionary forces upon a surgical robot and/or the surgeon to allow better control of the surgical instrument (for example, positioning thereof) during surgery. In addition to reducing the reactionary forces, it is also the purpose of this disclosure to mechanically provide all or a significant portion of the required forces to complete the surgery such that the surgeon and/or robot should only have to guide the tool with minimal force.

In an embodiment, the present disclosure provides for a rotary impacting tool for orthopedic surgery that is configured to minimize reactionary forces during large bone orthopedic surgery. The tool preferably comprises a mechanism (such as an absorbing means) that decreases the peak reactionary forces from the tool end that act on a gripping surface of the tool. Such gripping surface may include, but is not necessarily limited to, a hand grip or the like in the case of a tool that is designed for manual operation by a surgeon, or a cylindrical body or other mounting means in the case of a tool that is coupled to and operated by a surgical robot. It is to be understood that "surgical tool" and "impactor" refer to the invention disclosed herein, while "surgical implement" refers to attachments to the surgical tool's output. For example, surgical tool would refer to the rotary impact handpiece while surgical implement could refer to a semi-hemispherical reamer that attaches to the surgical tool output.

In an embodiment, the reactionary force is further reduced by using a dampening mechanism, which allows the reactionary force to be spread across a larger time period, thus reducing the reactionary force seen or felt at the gripping surface. In said embodiment, the dampening mechanism comprises a viscoelastic or non-Newtonian fluid disposed between the motor mount and the housing of the tool such that the reactionary torque is isolated from the tool housing and therefore from the surgeon/robot as well. It is obvious that this dampening mechanism can also be used to isolate the motor drive from the hammering mechanism and hence the location of this dampening mechanism can vary although its preferable location is between the gripping surface and the tool housing and/or the motor mount and the tool housing. In yet another embodiment, the tool may also comprise a counter movement element to absorb and spread reactionary forces across a longer time period.

In an embodiment, the tool comprises a torque sensing means, which torque sensing means, when a threshold torque value is reached or exceeded, may initiate a rotational impacting mechanism that transmits rotary impact force to the surgical implement. Said threshold torque value is preferably a torque lower than the torque which could damage the operating robot or surgeon's wrist. It has been discovered that the transition should occur around 30 to 50 inch pounds. The tool may then initiate a rotary impacting force on the impact hammer that is to be transmitted and/or translated to the surgical implement.

In yet another embodiment, the present disclosure provides for a rotary and linear impacting tool for orthopedic surgery that is configured to minimize reactionary forces during large bone orthopedic surgery. The tool may comprise a mechanism (such as an absorbing means) that decreases the peak reactionary forces from the tool end that act on a gripping surface of the tool. Such gripping surface may include, but is not necessarily limited to, a hand grip or the like in the case of a tool that is designed for manual operation by a surgeon, or a cylindrical body or other mounting means in the case of a tool that is coupled to and operated by a surgical robot. It is to be understood that "surgical tool" refers to the invention disclosed herein, while "surgical implement" refers to attachments to the surgical tool's output. For example, surgical tool may refer to the rotary/linear impact handpiece while surgical implement may refer to a semi-hemispherical reamer that attaches to the surgical tool output.

In an embodiment, an impactor or impacting tool comprises a hammer, an output anvil, and an energy storage means (which means may comprise, in an embodiment, a spring). The hammer and anvil are operatively coupled to and are capable of being rotated by a lead screw element (an example of such being a Torqsplinee). It is understood that the term "torqspline" is used in this disclosure as an exemplary embodiment of a lead screw element and as such the term "torqspline" should not be considered limiting. Upon rotation, when a sufficient load on the output anvil is reached, the output anvil and hammer may temporarily cease being rotated by the torqspline element, the hammer may translate up the torqspline, away from the object that is the target of impacting to energize the energy storage means until the hammer and output anvil are so aligned to allow the now-energized energy storage means to act on the hammer to allow the hammer to translate down the torqspline (while also rotating) to impact the output anvil with minimal reactionary torque.

The minimal reactionary torque is a result of two things: first, substantially decoupling the hammer from the output anvil. This restricts the reactionary torque to a certain threshold value dependent only on the energy storage means (a spring for example) and the pitch of the torqspline. Second, the sharp impact on the output anvil from the hammer allows the impact reamer to overcome a high load area (such as sclerotic bone/bone spurs in the acetabulum), with minimal reactionary torque to the surgeon. The high impact forces generated as a result of the impact of the hammer on the anvil breaks through the high load area, with minimal reactionary torque.

It is conceivable to those familiar in the art, that the translation and rotation of the hammer in the above-mentioned mechanism could be partitioned in such a way as to impart impacts in the both the rotary and linear direction simultaneously. It has been discovered that adding a linear impaction element to the reaming process increases the overall speed of the reaming stage while also reducing surgeon fatigue (the surgeon does not need to apply the linear push force that they do with a normal reamer. This push force can be in excess of 25 pounds). In an embodiment, impacting of the hammer in a linear direction is accomplished by an impact element that is disposed on the hammer and/or the output anvil, which element imparts or receives a linear impact when the hammer comes into contact with the output anvil as more specifically described elsewhere herein.

In an embodiment, the tool comprises a torque sensing means, which torque sensing means may cause rotational motion of the output anvil and/or hammer to cease.

In another embodiment, the surgical impacting tool comprises a hammer, an output anvil, and an energy storage means (which means may comprise, in an embodiment, a wave spring). The hammer and anvil are operatively coupled to and are capable of being rotated by a leadscrew (such as a torqspline screw) element. The tool further comprises a cam (such as a barrel) cam and cam follower and an impact rod. Rotation of the hammer may spin the anvil to have the anvil output a torque on the impact rod. The impact rod may turn the barrel cam, causing the wave spring to compress. After the cam follower clears the barrel cam, the wave spring can expand to force the cam and impact rod forward to generate a linear impact on the anvil.

In another embodiment, a rotary linear impactor or impacting tool comprises a hammer, an output anvil, and an energy storage means (which means may comprise, in an embodiment, at least one wave spring, and, in a further embodiment, a linear actuator spring and a rotary spring). The hammer and anvil are operatively coupled to and are capable of being rotated by a lead screw element (such as a torqspline). When the user pushes the output anvil into a bone surface, the anvil will also compress a linear actuator spring to provide for only rotary impaction or both rotary and linear impaction, depending on the amount of force with which the user pushes the output anvil into the bone surface.

DESCRIPTION OF THE DRAWINGS

The advantages and features of the present disclosure will become better understood with reference to the following detailed description and claims taken in conjunction with the accompanying drawings, wherein like elements are identified with like symbols, in which:

DETAILED DESCRIPTION OF THE DISCLOSURE

The exemplary embodiments described herein detail for illustrative purposes are subject to many variations in structure and design. It should be emphasized, however, that the present disclosure is not limited to a particular surgical tool, robot, robotic end effector, or any intermediaries as shown and described. That is, it is understood that various omissions and substitutions of equivalents are contemplated as circumstances may suggest or render expedient, but these are intended to cover the application or implementation without departing from the spirit or scope of the claims of the present disclosure. The terms "first," "second," and the like, herein do not denote any order, quantity, or importance, but rather are used to distinguish one element from another, and the terms "a" and "an" herein do not denote a limitation of quantity, but rather denote the presence of at least one of the referenced item.

The present disclosure provides for rotary linear impacting tools for orthopedic surgery and more specifically to those tools designed to minimize reactionary forces during large bone orthopedic surgery. As used herein, the tool may also be referred to as a rotary impactor or a combined rotary and linear impactor. A rotary impacting tool in this context may be understood to be a tool which effects constant rotary motion to a surgical implement and can further provide rotary impacts under certain conditions (i.e. if the reactionary torque reaches and/or exceeds a threshold value). The tool further may include a mechanism for generating a combined rotary and linear impact.

The tool as disclosed herein includes a mechanism (such as an absorbing means) which decreases the peak reactionary forces from the tool end that act on a gripping surface of the tool. Such gripping surface may include, but is not necessarily limited to, a hand grip or the like in the case of a tool that designed for manual operation by a surgeon, or a cylindrical body or other mounting means in the case of a tool that is coupled to and operated by a surgical robot. As used herein, "reactionary force" may include linear or rotary shock and/or force or torque reflected back to the robot and or surgeon mounting or gripping surface.

Figure 1:
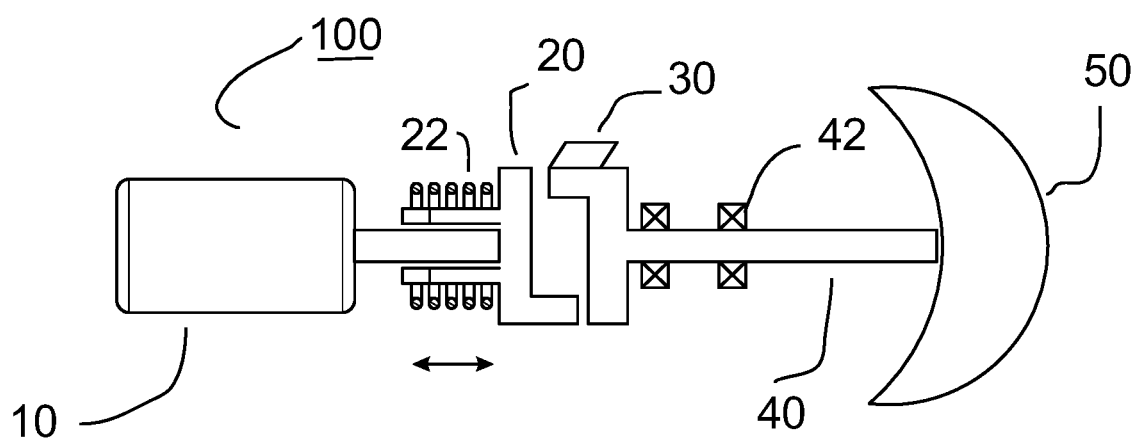
FIG. 1 shows a rotating hammer which is used to impart rotational movement of a surgical implement, in accordance with an exemplary embodiment of the present disclosure.

In an embodiment, and as shown in FIG. 1, the rotational action to the surgical implement 50 is communicated via an impact mechanism 20 such as a rotary hammer. In an embodiment, the tool 100 comprises a motor drive 10 that is operatively coupled to an impact bar (such as a rotary hammer 20). The motor 10 provides for rotational motion of the rotary hammer. The rotary hammer 20 is operatively coupled to a camming surface 30 through steel roller balls. The rotary hammer selectively engages an output anvil which output anvil can be coupled to an interface of the tool. Said interface is capable of receiving and rotating a surgical implement. The tool may also comprise at least one bearing 42 to maintain the output anvil 40 in a working position while it is acted on by the rotary hammer. The rotary hammer 20 rotates the output anvil until a threshold torque is reached on the output anvil. After said threshold torque is reached the roller balls pull the rotary hammer back against spring 22 until the rotary hammer is no longer in contact with the output anvil. At this point the rotary hammer is accelerated to a higher velocity and a spring 22 pushes the rotary hammer forward to allow the hammer to reengage and rotationally impact the output anvil.

It was discovered that by putting a reduction means between the rotary impacting mechanism and the output improves the safety profile of the existing rotary impact mechanisms without sacrificing output impact energy. This discovery allows for torque multiplication while leaving the maximum rpm of the output at a reasonable speed and avoiding the possibility of excessive rotational speed at the output (which can otherwise cause body fluids to be splattered in the operating room, cause uncontrolled reaming and soft tissue damage).

Figure 13:
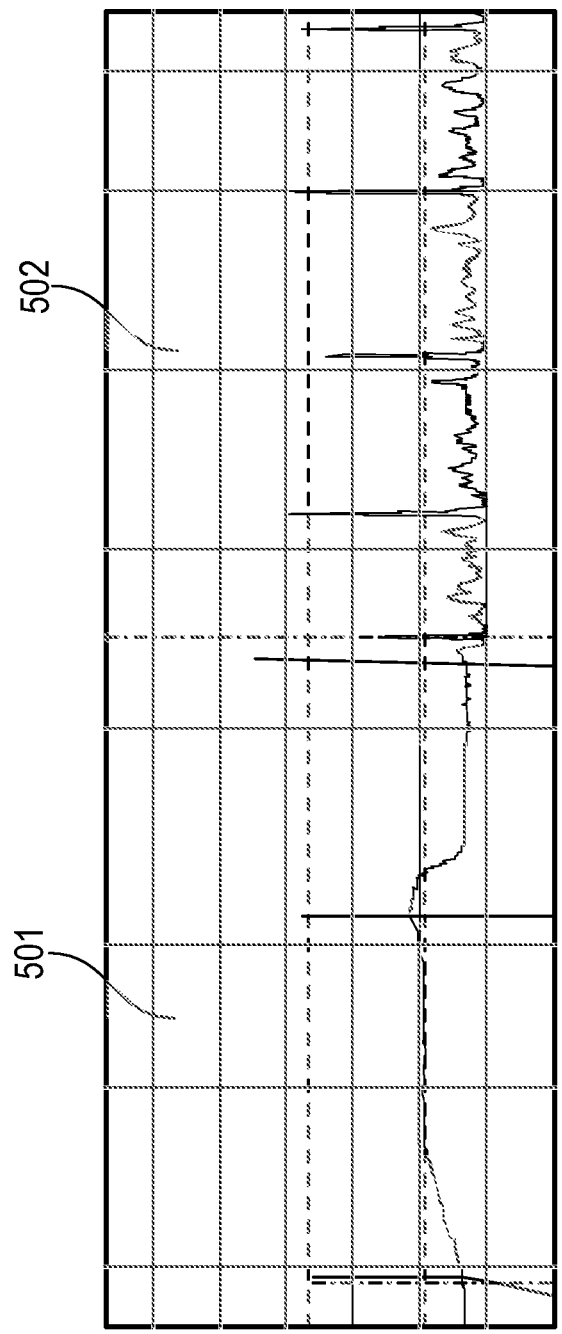
FIG. 13 shows a comparison of the force applied to the back of a typical surgical reamer and the linear force imparted by an exemplary embodiment of a linear and rotary impactor.

In an embodiment, the output anvil 30 has the ability to move linearly along the impact axis. The spring 22 can impart a linear impact by moving the rotary hammer 20 so that a face of the rotary hammer 23 contacts a face of the output anvil 24 and transfers energy from spring 22 in a linear direction whilst the hammer is also causing a rotary impact. In this embodiment, said spring can be allowed to translate through the output anvil such that a linear impact is also effected on the surgical implement. The advantage of linear impaction during the reaming process is illustrated in FIG. 13. Curve 501 shows the typical constant force that is imparted on the back of a reamer handpiece by a surgeon during the reaming process (typically in excess of 25 pounds). Curve 502 shows the sharp linear impacts imparted on the surgical site by the linear impaction mechanism as disclosed herein. The benefit of high frequency linear impacts is that the surgeon and/or robot does not have to provide the same external push force on the back of the tool in order to perform a successful surgical operation.

Figure 2:
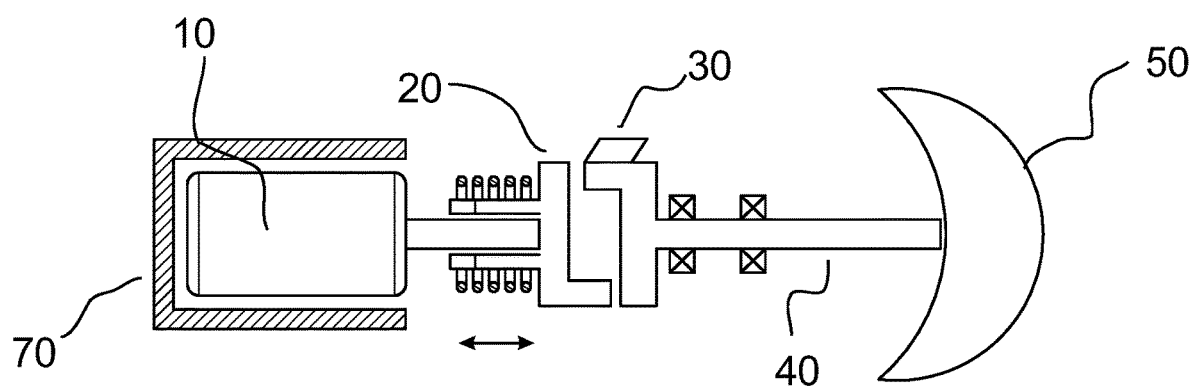
FIG. 2 shows a dampening mechanism which reduces the reflected impulse to the surgeon and or surgical robot, in accordance with an exemplary embodiment of the present disclosure.
Figure 4:
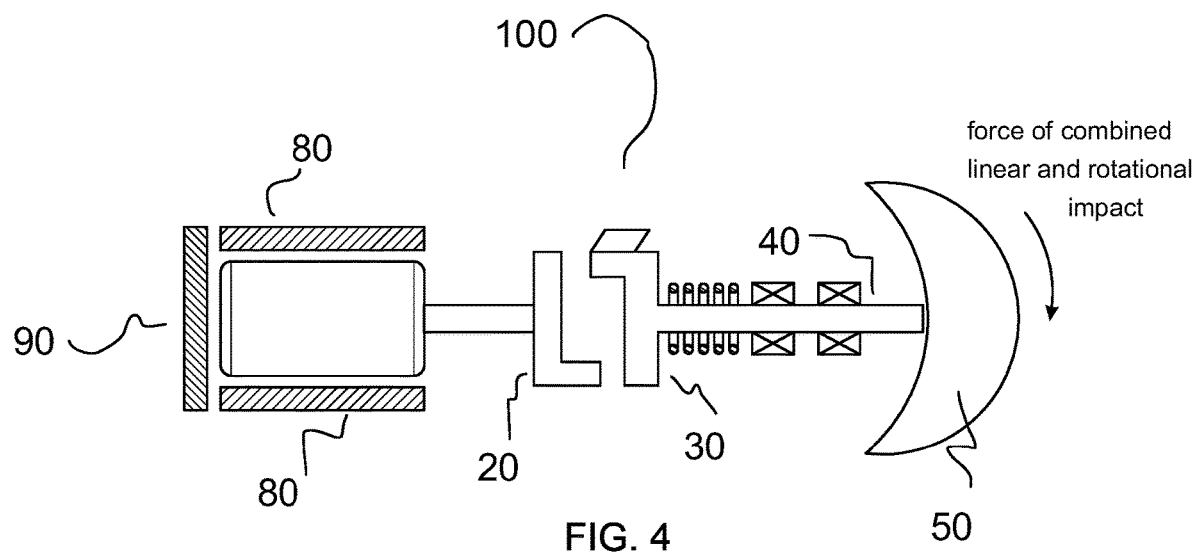
FIG. 4 shows a dampening mechanism which reduces the reflected impulse to the surgeon and or surgical robot from both the rotating and linear impaction, in accordance with an exemplary embodiment of the present disclosure.

In an embodiment as shown in FIG. 2, a viscoelastic mechanism or a dampening mechanism 70 is used to reduce the reflected force and or torque during operation of the surgical impacting tool. The mechanism 70 may be disposed on, around, or in proximity to the motor 10 of the tool 10 such that some rotational freedom of movement is permitted, however, the mechanism 70 will also have a rotational spring constant to allow for predictable compensation and dampening as well as recovery between impacts by the impact hammer 20. It will be apparent that this mechanism 70 may also be incorporated in the rotational impacting tool described further below herein. Referring to FIG. 4, a dampening mechanism 80 and 90 may be provided to reduce the reflected rotary and/or linear force of the impacting tool.

In a still further embodiment, the tool comprises one or more sensors 39 which establish spatial location with respect to the patient. In a still further embodiment, the measurements that determine spatial location are coordinated with the impacts such that the tool has recovered to at least 90% of its pre-impact position prior to communicating the tool position to either the robot or other device. It is apparent that this sensor-measurement integration system is advantageous because it makes efficient use of computing power by only taking measurements when needed and because it gathers and communicates only the most accurate and useful location data.

Figure 3:
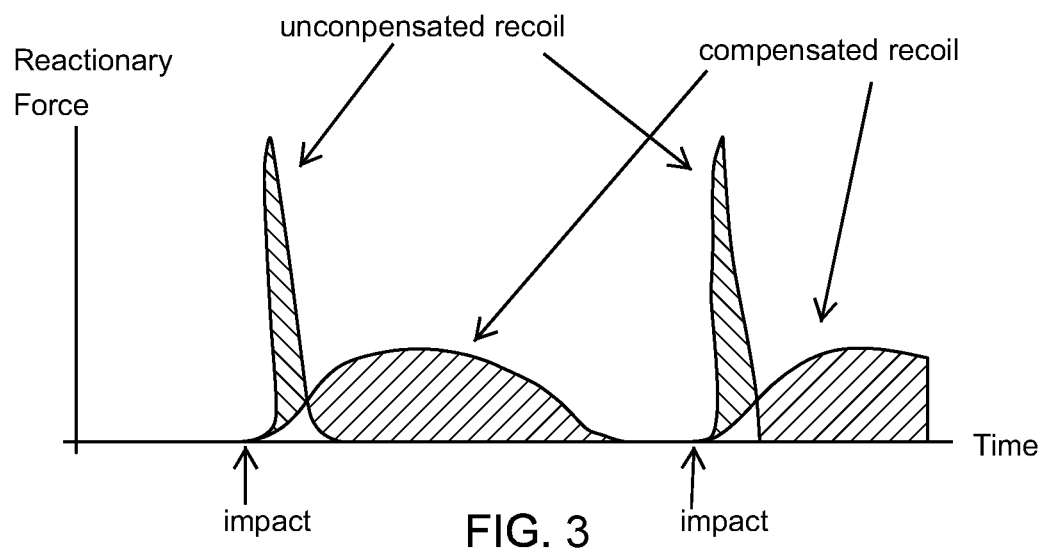
FIG. 3 shows a sample calculation of reactionary force reduction by expanding the time period over which that force is applied in accordance with an exemplary embodiment of the present disclosure.

In an embodiment, the tool is designed in such a fashion as to isolate the tool function from the recoil or reactionary force by using a "free flight impacting member". The free flight (or thrown) member, as used herein, is a moving member of and within the tool, a portion of which movement is in free flight with respect to the tool. The impact of the thrown member onto a receiving member imparts a consistent force onto the surgical implement of the tool (for example, the output 40) but equally important is the fact the launching of the thrown member is a predictable impulse which can be compensated for by a sleeve, slide cage or the like. In an embodiment, the reactionary force that is seen at the gripping surface is reduced by extending the time period (as shown in FIG. 3) over which the thrown member impacts a surface. This is accomplished through conservation of momentum (m w1=m2v2), which can also be written in terms of impulse as F1l1t1=F2l1b (where F is force and 1lt is the time period over which that force occurs). Although the equation is for linear momentum, this concept applies to rotational momentum as well.

Referring now to FIG. 3, a sample calculation of reactionary force reduction by expanding the time period over which that force is applied is shown, as in accordance with an exemplary embodiment of the present disclosure. In an embodiment, the reactionary force that is generated by the impact hammer may be reduced by extending the time period (as shown in FIG. 4) over which the force is imparted on to the motor mount or gripping surface, for example. This occurs due to the law of conservation of momentum as discussed above. The time period (11t) can be extended by using a viscoelastic mechanism or dampening mechanism 70 between the motor mount and the tool housing or between the gripping surface and the tool housing, for example.

In another embodiment as shown in FIG. 4, the rotational action of the tool 100 can be combined with a linear action. Linear impacts as contemplated by this disclosure comprise a throw that is less than 1 mm per impact, which impacts are performed in the early stages of reaming the acetabulum. It was unexpectedly discovered that adding a small linear impact in combination with the rotary impact reduced the linear force needed by the surgeon by over 50% in the initial reaming of the acetabulum. In an embodiment, the motor 10 causes both linear and rotational motion of the hammer 20. In such an embodiment the camming surface(s) 30 may comprise a linear ramp for permitting the force of linear (or axial) motion of the impact bar 20 to be translated to the output 40 (and surgical implement 50) and a rotary ramp for permitting the force of rotary motion of the hammer 20 to be translated to the output 40 (and surgical implement 50). In an embodiment, the tool further comprises a spring, which spring may be compressed when the camming surface for linear impacting causes the hammer to translate away from the output. The spring may be compressed by the translation of the hammer. After the hammer disengages from the linear ramp of the camming surface, the spring acts on the hammer to move the hammer in a linear direction to impact the output. The tool 100 may further comprise bearings 42 for facilitating rotational and linear motion of the output 40. In an embodiment, the tool 100 may permit selection (by way of a switch 36, for example) of translation of both linear and rotational force by the hammer 20 to the output 40, and of translation of only rotational force to the output 40. In an embodiment, the linear impact is limited to less than 0.5 mm per revolution of the arbor of the tool.

In an embodiment, the tool has the capability to determine the stiffness of the impact site (i.e. surgical site) by measuring the force of an impact as it relates to the change in either linear and/or rotary displacement. For example, the tool might count 10 impacts from the rotary hammer and determine (such as through a sensor) that the reamer has only moved by 0.1 degree rotationally and 0.001" linearly over that period of impacts. The tool may thereupon indicate to the surgeon/robot (through a status light, sound or a pause or slowing of the tool's operation) that the reamer is no longer advancing and a decision could be made by either the surgeon or the robot to continue or cease impacting.

In a further embodiment and as shown in FIG. 2, the gripping or mounting surface can be lined with a force-absorbing sleeve or sleeves 80, which may be made from a material (such as Sorbothane). This can be used to absorb and spread the reactionary forces over a long time period thus reducing the reactionary force of the tool on the surgeon and or robot In an embodiment, the tool comprises an internal absorption means, which internal absorption means comprises a shock absorbing material such as urethane (including but not necessarily limited to Sorbothane and viscose), for example. In a further embodiment the internal absorption means comprises a dampening material and or mechanism and a spring restoration mechanism. In a still further embodiment, such a mechanism may be combined in a single material such as a shock absorbing urethane, rubber, foam, plastic or the like. Such a single material is not limited to a nonmetal.

In another embodiment, the internal absorption means includes a fluidic dampening system.

In an embodiment, the rotary impacting tool comprises an overload clutch as to limit the reactionary torque seen by the body of the tool.

Figure 5:
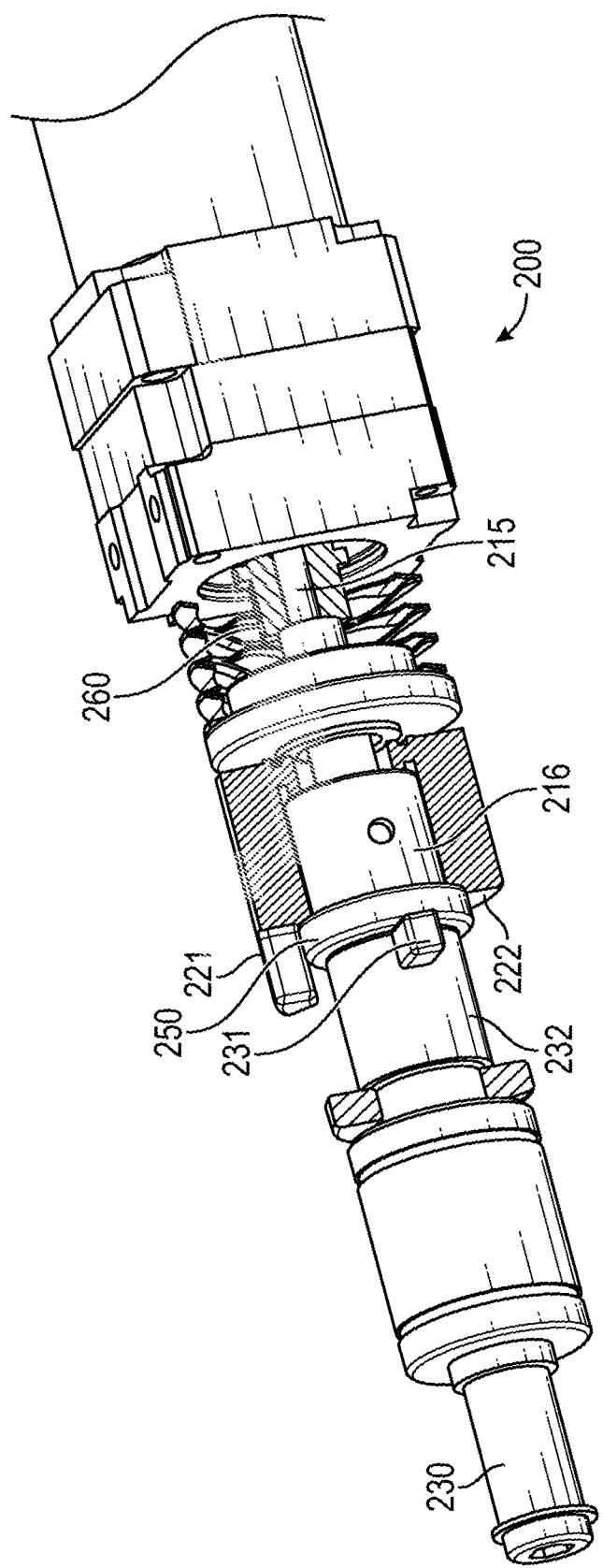
FIG. 5 shows a cutaway view of an orthopedic impacting tool, in accordance with an exemplary embodiment of the present disclosure.
Figure 6:
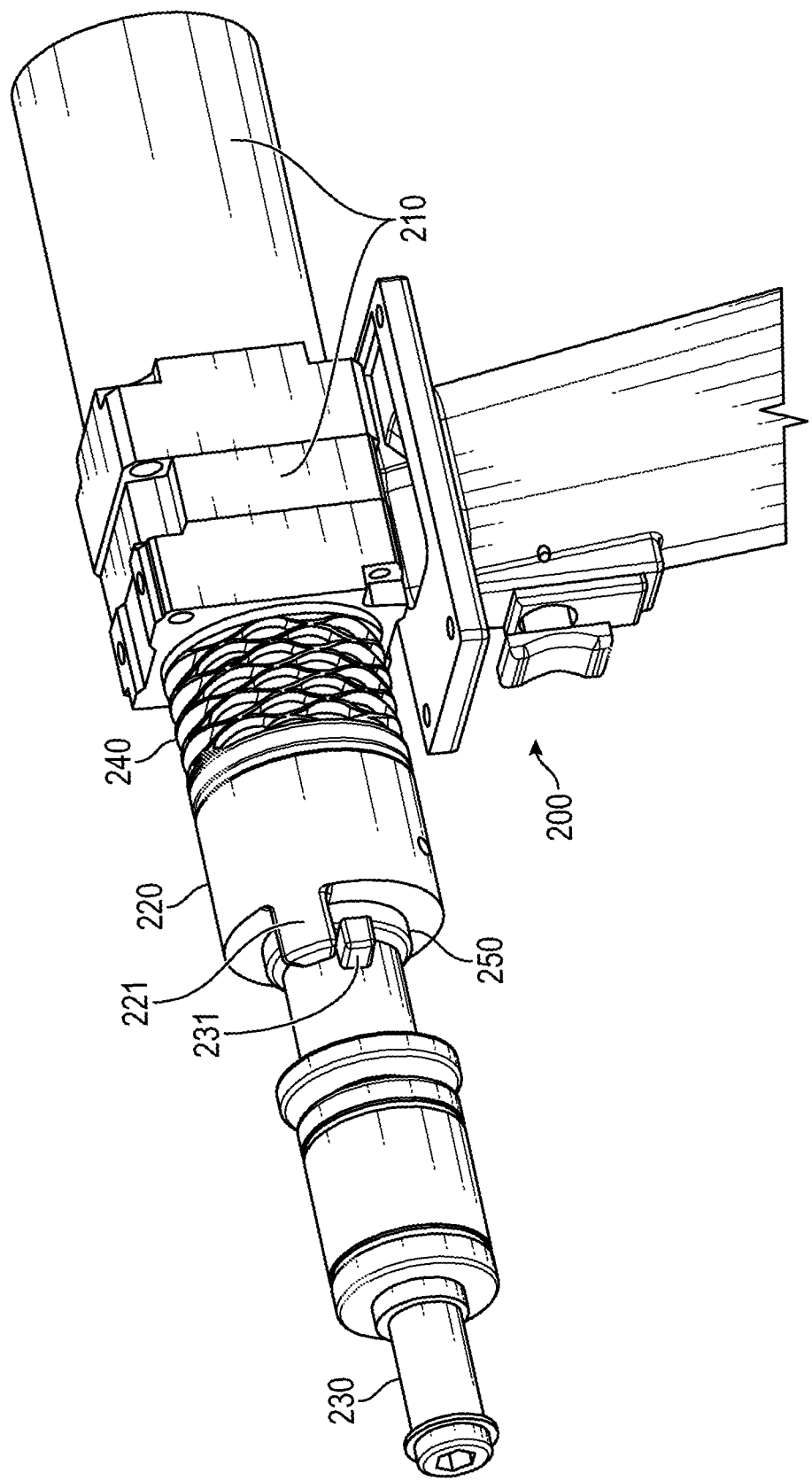
FIG. 6 shows an exemplary hammer and an exemplary output anvil of an orthopedic impacting tool, in accordance with an exemplary embodiment of the present disclosure.

In yet another embodiment, and as shown in FIGS. 5 and 6, a rotary linear impacting tool 200 that features rotational and linear movement is shown, which movement allows a hammer 220 to strike an output anvil 230, which output anvil 230 then may deliver an impact to a surgical area, for example. In an embodiment, the tool 200 comprises a motor and gearbox 210 that is operatively coupled to a leadscrew such as a torqspline 215. The motor provides for rotational motion of the torqspline. The torqspline 215 includes a lead nut 216, which lead nut 216 rotates when the torqspline 215 rotates and the delivered torque to the anvil is below the threshold torque for impacting. The hammer 220 is operatively coupled to the lead nut 216 such that the hammer rotates along with the lead nut 216. As the hammer 220 rotates, it may selectively engage and rotate the output anvil 230.

In an embodiment, the hammer 220 comprises at least one tooth or other protrusion 221 that extends longitudinally away from the face 222 of the hammer 220. In an embodiment, the output anvil 230 comprises at least one tooth or other protrusion 231 that extends away laterally from the body 232 of the anvil. In an embodiment, the at least one tooth (or protrusion) 221 of the hammer may engage the at least one tooth (or protrusion) 231 of the output anvil 230 such that while the hammer 220 rotates, such engagement causes the output anvil 230 to rotate. The rotation may continue until a sufficiently high load is imparted on the output anvil 230, such that the output anvil 230 ceases rotating. This causes the hammer 220 to also stop rotating due to the still-engaged protrusions 231 and 221, respectively of the output anvil 230 and hammer 220.

In an embodiment, the impact tool 200 further comprises an energy storage means 240 (such as a die spring, for example) and a lead screw element (an exemplary example of which is a torqspline 215). In an embodiment, the die spring 240 is disposed between the lead nut 216 and the motor 210 of the tool 200. It will be apparent that the coil of the spring facilitates placement of the spring 240 around the torqspline 215. In an embodiment, the torqspline is constantly rotating. In such an embodiment, and when the hammer 220 ceases rotation, the lead nut 216 and hammer 220 to which it is attached will translate backwards (away from the output anvil 230). Such backward translation of the lead nut 216 and hammer 220 causes the die spring 240 to compress. The translation and compression continue until the hammer 220 has moved a sufficient backward distance such that the at least one protrusion 221 of the hammer 220 has disengaged from the at least one protrusion 231 of the output anvil 230.

Once the hammer 220 has moved a sufficient distance backward such that its at least one protrusion 221 has disengaged from the at least one protrusion 231 of the output anvil 231, the hammer teeth slide along the anvil teeth until they clear the anvil teeth and the spring 240 decompresses to force a high-speed rotational movement of the hammer 220 down the torqspline 215 toward the output anvil 230. This high-speed rotational movement of the hammer 220 will cause a sharp rotational impact upon the anvil which sharp force is sufficient for the impact tool 200 to overcome the bone structure or malformity that has impeded the reaming action. In an embodiment, the motor 210 can be programmed to increase its speed when the hammer 220 is pulling back (which indicates that the threshold torque has been reached and a rotary impact is set to occur). This has the advantage of maintaining a constant output RPM whether in the rotary impacting stage or the constant rotation stage.

Such an impact mechanism allows much higher rotational torque to be achieved in reaming as compared to conventional orthopedic reaming tools. This improvement is at least 200% and the reduction of reactionary torque is over 2× that which can be achieved with conventional orthopedic reaming tools. In an unexpected discovery, the tool was discovered to switch from impact mode (which has an auditory signal resulting from the impacts) to a non-impact mode (minimal auditory signal) at or near the completion of the surgical reaming.

When the hammer 220 is forced down the torqspline 215 due to the decompression of the spring 240, there is linear energy as well as rotary energy available from the hammer 220. In an embodiment, a compression element 250 is provided to facilitate transmission of a linear impact and force from the hammer 220 to the output anvil 230. The compression element 250 is preferably disposed between the face 222 of the hammer and the output anvil 230. In an embodiment, the face 222 of the hammer 220 impacts the body 232 of the output anvil 230 as the hammer 220 translates down the torqspline 215 as a result of decompression of the spring 240. In an embodiment, the compression element 250 comprises an elastomeric material friction disk. In such an embodiment, element 250 absorbs a portion of the rotational energy of the hammer 220 and translates that energy into a linear force that acts on the output anvil 230.

In a still further embodiment, the tool 200 comprises one or more sensors (not shown) which establish spatial location with respect to the patient. In a still further embodiment, the measurements which determine spatial location are coordinated with the impacts such that the tool 200 has recovered to at least 90% of its pre-impact position prior to communicating the tool position to either the robot or other device. It is apparent that this sensor-measurement integration system is advantageous because it makes efficient use of computing power by only taking measurements when needed and because it communicates only the most accurate location data.

In an embodiment, the tool 200 has the capability to determine the stiffness of the impact site (i.e. surgical site) by measuring the force of an impact as it relates to the change in either linear and/or rotary displacement. For example, the tool 200 might count ten (10) impacts from the output anvil 230 and determine that the reamer has only moved by 0.1 degree rotationally and 0.001" linearly over that period of impacts. The tool 200 could indicate to the surgeon/robot that the reamer is no longer advancing and a decision could be made by either the surgeon or the robot. In an embodiment, the tool 200 comprises an internal absorption means (not shown) which may be internal to the housing of the tool or at the gripping or mounting surface of the tool and may comprise a shock absorbing elastomer material such as urethane Sorbothane or viscose.

Figure 7:
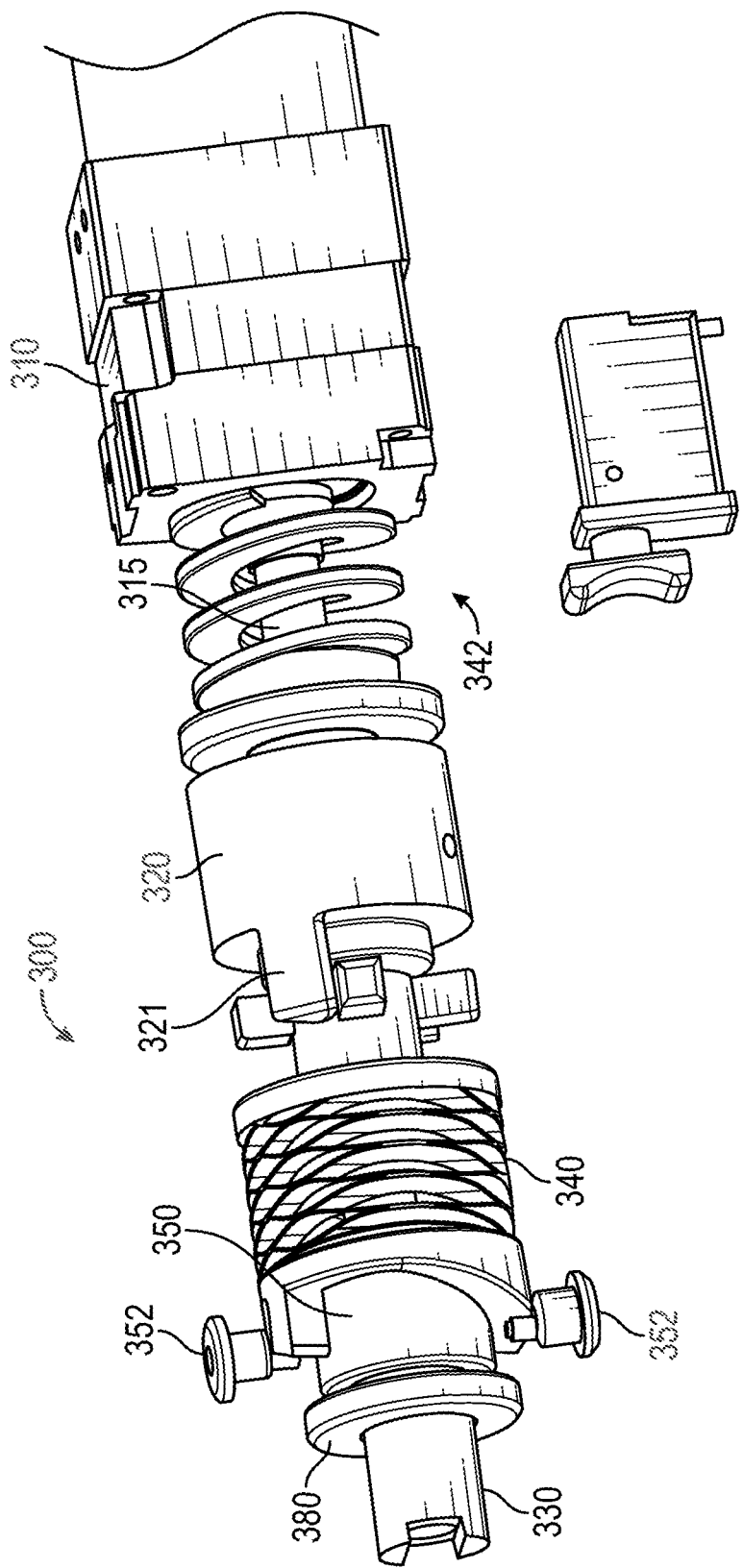
FIG. 7 shows a linear and rotary impactor comprising a cam in accordance with an exemplary embodiment of the present disclosure.
Figure 8:
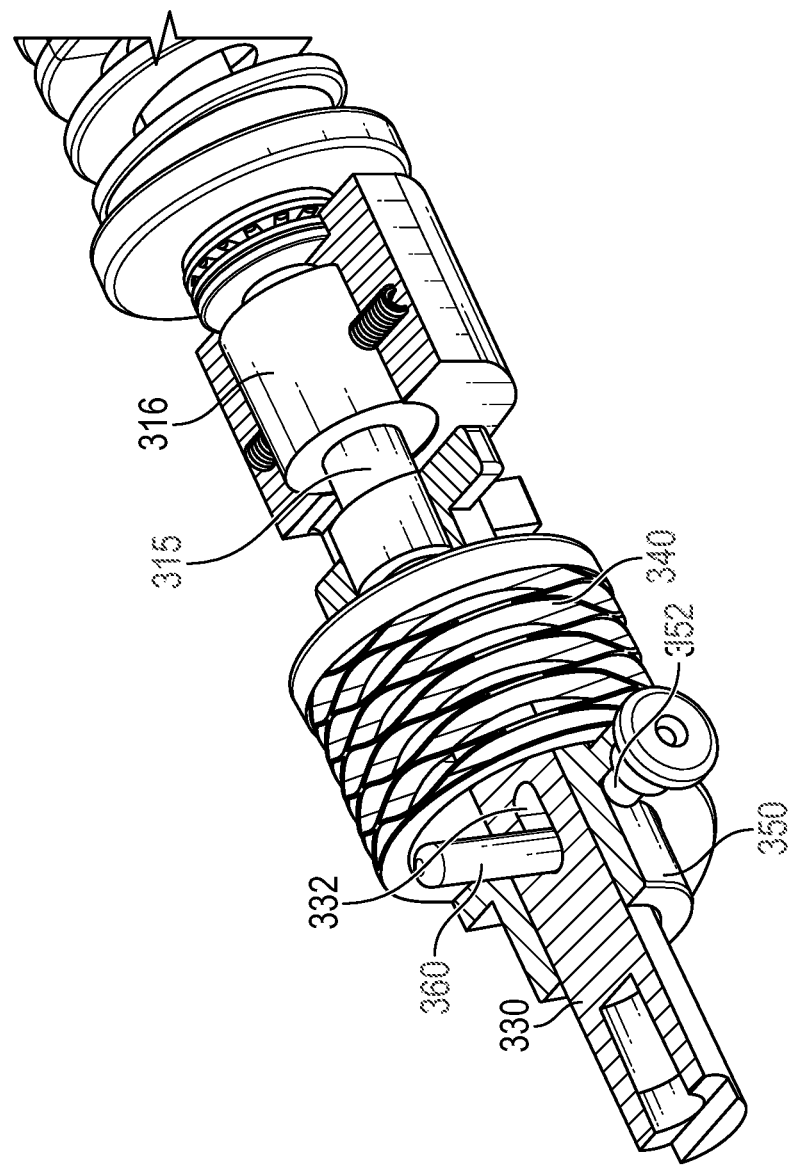
FIG. 8 shows another view of a linear and rotary impactor comprising a cam and impact bar in accordance with an exemplary embodiment of the present disclosure.
Figure 9:
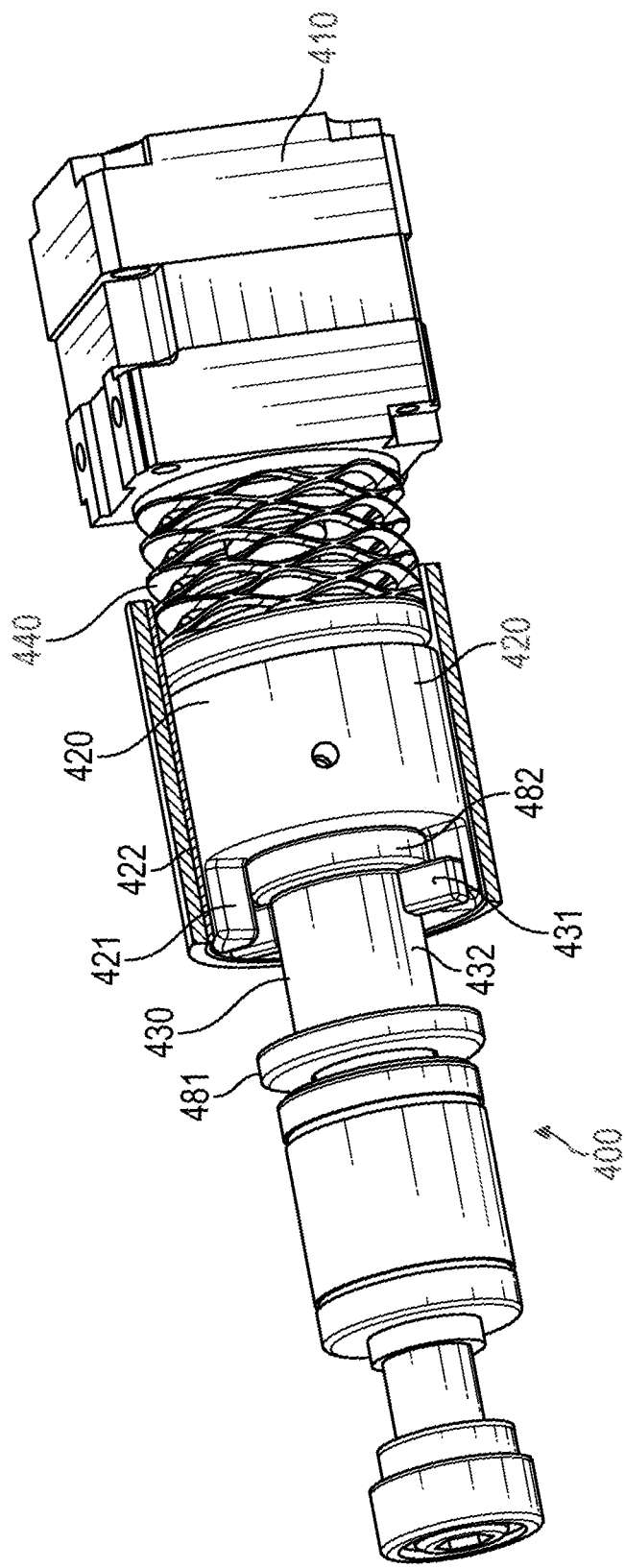
FIG. 9 shows a linear and rotary impactor comprising at least one bumper in accordance with an exemplary embodiment of the present disclosure.
Figure 10:
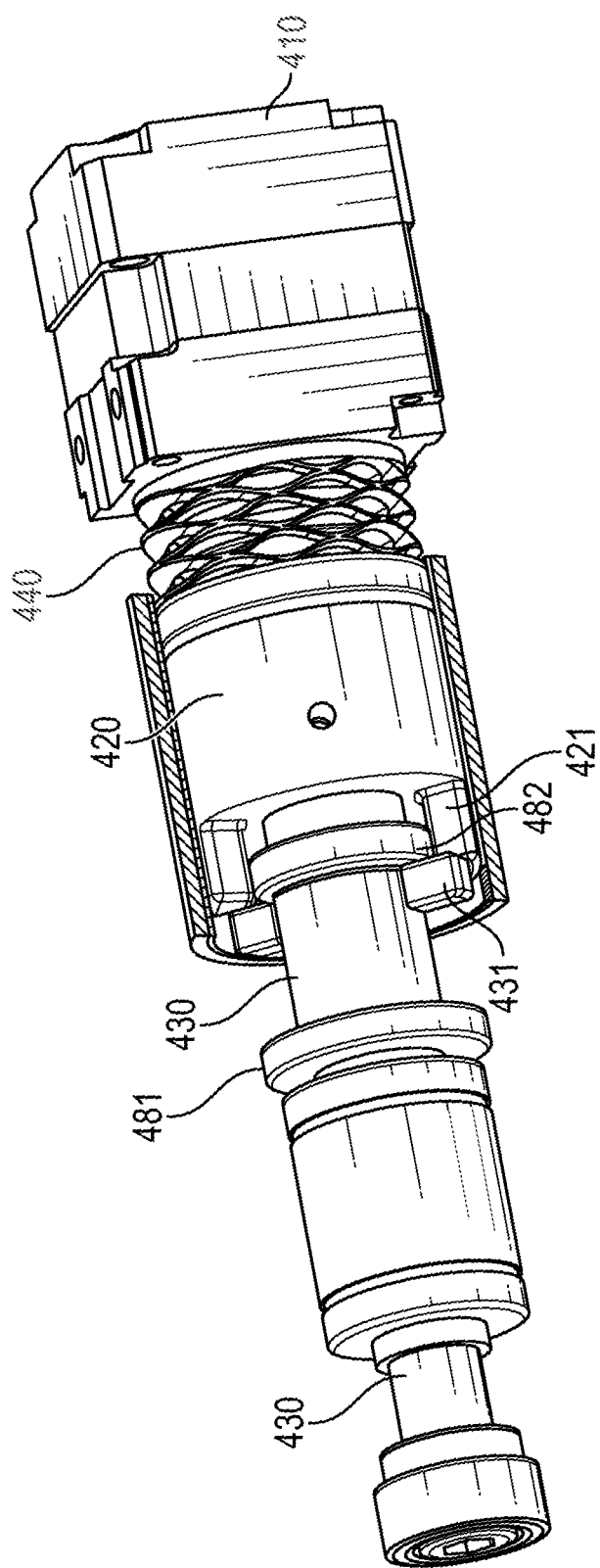
FIG. 10 shows a linear and rotary impactor comprising at least one bumper in accordance in position to impart an impact on the output in accordance with an exemplary embodiment of the present disclosure.
Figure 11:
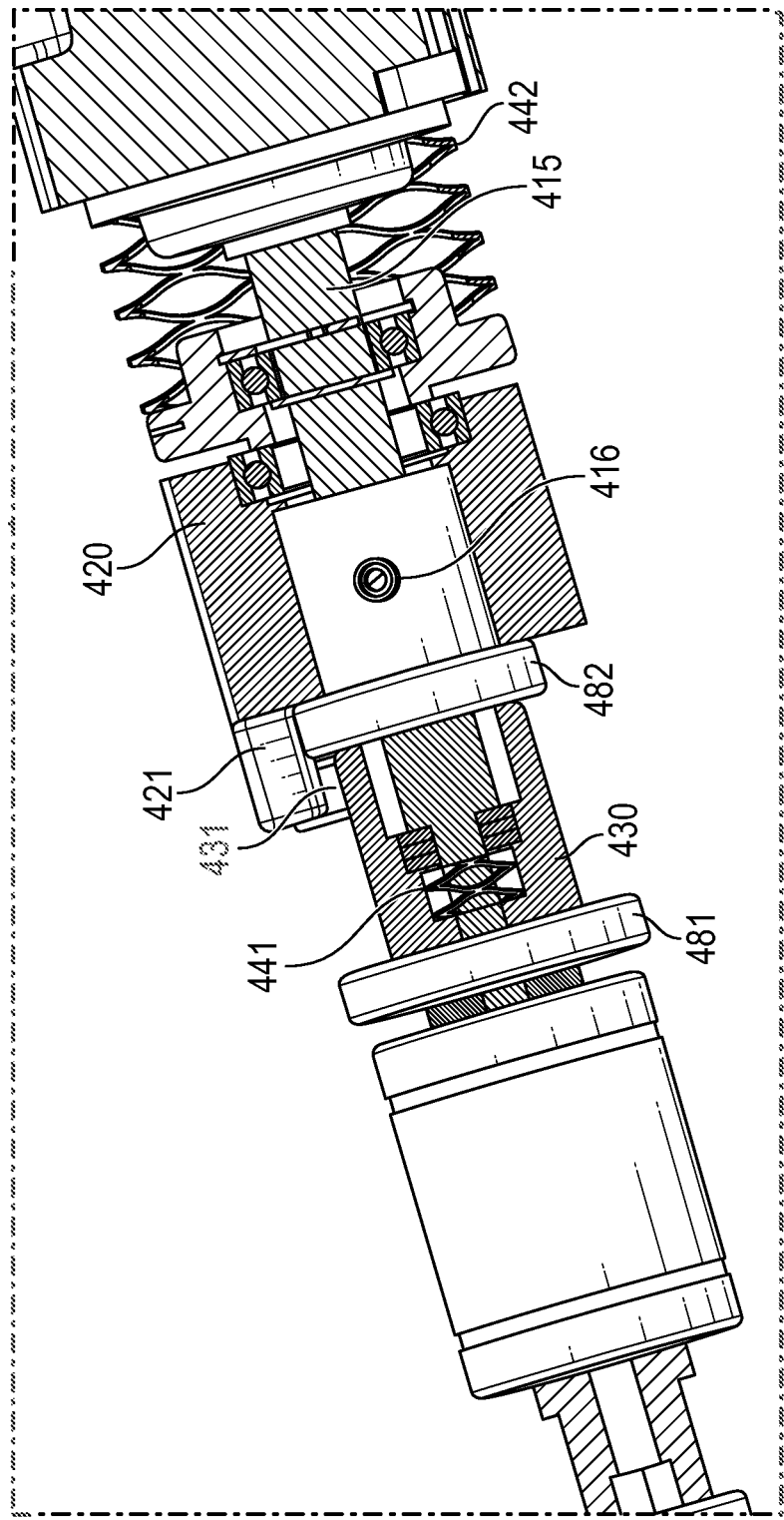
FIG. 11 shows a linear and rotary impactor comprising at least one bumper in accordance with another exemplary embodiment of the present disclosure.
Figure 12:
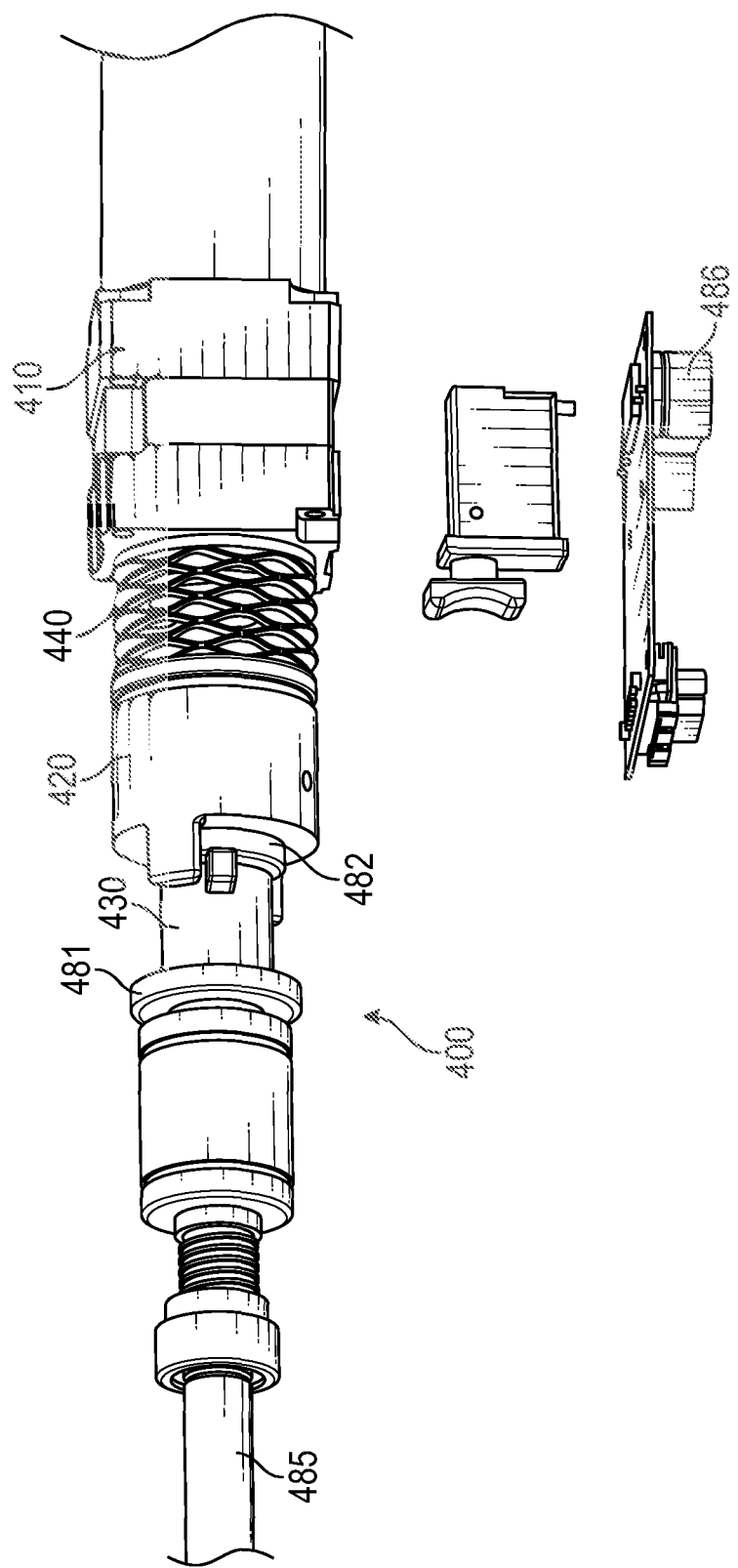
FIG. 12 shows a linear and rotary impactor comprising at least one bumper in accordance with another exemplary embodiment of the present disclosure.

In another embodiment, and as shown in FIGS. 7 and 8, a rotary linear impacting tool 300 comprises a motor 310, a hammer 320, an output anvil 330, and a linear energy storage means 340 (which means may comprise, in an embodiment, a wave spring) and a rotary energy storage means 342. The hammer and anvil are operatively coupled to and are capable of being rotated by a leadscrew such as a torqspline 315 The tool further comprises a cam 350 (such as a barrel cam) and at least one cam follower 352 and an impact rod 360. The impact rod 360 is at least partially contained within the cam 350 and is capable of imparting a rotational force on the cam to cause the cam to rotate or cycle. The tool 300 further comprises at least one bumper 380. The anvil 330 comprises a slot 332 to accommodate and allow linear movement of the cam 350 and impact rod 360 with respect to the anvil 330.

In this embodiment, rotary impaction by the tool 300 is accomplished similar to the rotary impaction performed by tool 200 disclosed elsewhere herein. In an embodiment, motor 310 provides for rotational motion of the torqspline 315. The torqspline 315 includes a lead nut 316, which lead nut 316 rotates when the torqspline 315 rotates. The hammer 320 is operatively coupled to the lead nut 316 such that the hammer rotates along with the lead nut 316. As the hammer 320 rotates, it will selectively engage and rotate the output anvil 330 and may or may not impart impacting depending on the threshold torque.

For linear impaction by the tool 300, impact rod 360 is disposed partially within the anvil 330 and is further operatively coupled to the cam 350. Rotation of the anvil 330 (caused by rotation of hammer 320) outputs a torque on the impact bar 360, which torque causes the barrel cam 350 to rotate.

The cam follower 352 is operatively coupled to the barrel cam as well as to the wave spring 340. When the barrel cam 350 rotates, the cam follower 352 follows the track of the barrel cam and compresses the wave spring 340 in the process to store potential energy in the spring. The slot in the anvil 330 allow the impact rod 360 and the barrel cam 350 to move linearly with respect to the anvil 330 during this operational phase. After the cam follower 352 clears the track of the barrel cam 350, the wave spring releases the stored energy to force the cam 350 and impact rod 360 in the direction of the surgical site. The cam and rod impact the anvil 330 such as at the end of the anvil slot 332 that is proximate to the surgical site, thereby imparting a linear impact force to the output of the tool. A bumper 380 may be provided as shown in FIG. 7 to limit the linear travel of the anvil 330 for reduced recoil and increased control of the tool.

In another embodiment and as shown in FIGS. 9, 10, 11 and 12, a rotary linear impacting tool 400 comprises a motor 410, a hammer 420, an output anvil 430, and an energy storage means 440 which means may comprise, in an embodiment, at least one wave spring. The hammer 420 and anvil 430 are operatively coupled to and are capable of being rotated by a lead screw element (such as torqspline 415). The tool 400 may include at least one bumper such as a stop bumper 481 and an impact bumper 482. The stop bumper is preferably disposed between anvil 430 and the housing. Impact bumper 482 may be disposed on the end of the anvil 430 that is contacted by the hammer 420 for example. When the surgeon or robot pushes the surgical implement 485 which is coupled to the anvil onto a bone surface, the anvil will compress at least one spring 440 (and, in an embodiment, linear actuator spring 441 and rotary spring 442), which will allow for linear impaction as well as rotary impaction.

In this embodiment, rotary impaction by the tool 400 is accomplished similar to the rotary impaction performed by tool 200 and tool 300 disclosed elsewhere herein. In an embodiment, motor 410 provides for rotational motion of the torqspline 415. The torqspline 415 includes a lead nut 416, which lead nut 416 rotates when the torqspline 415 rotates. The hammer 420 is operatively coupled to the lead nut 416 such that the hammer rotates along with the lead nut 416. As the hammer 420 rotates, it will selectively engage and rotate the output anvil 430.

In an embodiment, the hammer 420 comprises at least one tooth or other protrusion 421 that extends longitudinally away from the face 422 of the hammer 420. In an embodiment, the output anvil 430 comprises at least one tooth or other protrusion 431 that extends away laterally from the body 432 of the anvil. In an embodiment, the at least one tooth (or protrusion) 421 of the hammer may engage the at least one tooth (or protrusion) 431 of the output anvil 430 such that while the hammer 420 rotates, such engagement causes the output anvil 430 to rotate. The rotation may continue until a sufficiently high load is imparted on the output anvil 430 (such as, in the course of surgical reaming, the tool encounters a bone spur), such that the output anvil 430 ceases rotating. This causes the hammer 420 to also stop rotating due to the still-engaged protrusions 431 and 421, respectively of the output anvil 430 and hammer 420.

In an embodiment, the spring 440 is disposed between the lead nut 416 and the motor 410 of the tool 400. In an embodiment, spring 440 comprises a wave spring. It will be apparent that the coil of the spring 440 facilitates placement of the spring 440 around the torqspline 415. In an embodiment, the torqspline is constantly rotating. In such an embodiment, and when the hammer 420 ceases rotation, the lead nut 416 and hammer 420 to which it is attached will translate backwards (away from the output anvil 430). Such backward translation of the lead nut 416 and hammer 420 causes the rotary 440 to compress. The translation and compression continue until the hammer 420 has moved a sufficient backward distance such that the at least one protrusion 421 of the hammer 420 has disengaged from the at least one protrusion 431 of the output anvil 430 as shown in FIG. 16.

Once the hammer 420 has moved a sufficient distance backward such that its at least one protrusion 421 has disengaged from the at least one protrusion 431 of the output anvil 431, the hammer continues to rotate until its teeth slide past the anvil teeth and then rotary spring 442 decompresses to force a high-speed rotational movement of the hammer 420 down the torqspline 415 toward the output anvil 430 and impact bumper 482. This high-speed rotational movement of the hammer 420 will cause a sharp rotational impact upon the at least one protrusion 431 of the output anvil 430, which sharp force upon the output anvil 430 should be sufficient for the impact tool 400 to overcome the bone structure or malformity that has impeded the reaming action. In an embodiment, the motor 410 can be programmed to increase its speed when the hammer 420 is pulling back (which indicates that the threshold torque has been reached and a rotary impact is set to occur). This would be beneficial to maintain a constant output RPM whether in the rotary impacting stage or the constant rotation stage.

When the hammer 420 is forced down the torqspline 415 due to the decompression of the rotary spring 442, there may be linear energy as well as rotary energy available for the anvil 430 for impacting a surgical site. That is, depending on the extent of compression of the linear actuator spring 441 prior to the hammer moving down the torqspline the tool may impart both a linear and rotational impact on the anvil 430. In an embodiment, an impact bumper 482 facilitates transmission of a linear impact and force from the hammer 420 to the output anvil 430. In an embodiment, the face 422 of the hammer 420 impacts the impact bumper 482 which transmits the linear impact to the anvil 430 as a result of decompression of the rotary spring 442.

It will be apparent that the linear actuator spring 441 may be compressed by the user and/or by the mass of the tool 400 when the tool 400 is placed against the surgical site. The user may increase the compression of the spring 441 by applying additional pressure on the tool 400 as it is disposed against the surgical site. If the spring 441 is sufficiently compressed that it does not have time (dependent on the spring constant of this spring) to expand before the linear impact and force from the hammer 420 is transmitted to the output anvil 430, the anvil 430 will receive and transmit the linear force to the surgical site. If the linear actuator spring 441 is insufficiently compressed before the hammer 420 transmits its rotational energy to the output anvil 430, the energy is absorbed rotationally or through the stop bumper 481.

The present disclosure offers the following advantages: reduction of reactionary forces from a surgical tool to the gripping and or mounting surface. Another advantage is that the tool will provide a significant amount of the forces required to complete a surgery without the need for external forces (for example, the external force from a surgeon that leans into the reamer handpiece to get the reamer to advance in the surgical site). This results in less wear and tear on a robotic platform in the case of robotic surgery and less surgeon fatigue for a surgeon operator. This also improves the accuracy and capability of the robot in the case of a robotic surgical tool and may drastically reduce instances of a loss of registration by a surgical robot.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The exemplary embodiment was chosen and described in order to best explain the principles of the present disclosure and its practical application, to thereby enable others skilled in the art to best utilize the disclosure and various embodiments with various modifications as are suited to the particular use contemplated.

What is claimed is:

1. A rotary and linear impacting tool, the tool comprising:
   a motor;
   an impact hammer;
   an output anvil; and
   an energy storage portion including a lead screw and a mechanical spring,
   wherein the impact hammer is energized by the energy storage portion and thereafter moves to impart at least one of a rotary force and a linear force on the output anvil,
   wherein a speed of the motor adjusts to maintain a constant output revolutions per minute (RPM) while operating rotationally or rotationally impacting.

2. The tool of claim 1, wherein the energy storage portion is proximate to the impact hammer for a portion of an operational cycle of the tool.

3. The tool of claim 1, wherein the impact hammer is energized by the energy storage portion in response to a torque exceeding a threshold.

4. The tool of claim 1, further comprising:
   a surgical implement.

5. The tool of claim 4, further comprising:
   a dampener, wherein the dampener reduces a reactionary torque to less than a predetermined percentage of a peak torque applied to the surgical implement.

6. The tool of claim 5, wherein the predetermined percentage of the peak torque is 50%.

7. The tool of claim 1, wherein a linear impact is limited to a stroke of less than two millimeters per impact.

8. The tool of claim 1, wherein a transition between impacting and non-impacting includes an audible signal.

9. The tool of claim 1, further comprising:
   a sensor, wherein the sensor identifies whether a forward progress of the tool is less than a predetermined distance in a predetermined number of impacts or time.

10. The tool of claim 9, wherein, in response to the sensor identifying that the forward progress is less than the predetermined distance in the predetermined number of impacts, the tool shuts off, slows down, emits light, or otherwise provides a cue.

11. The tool of claim 1, further comprising:
    a sensor, wherein the sensor determines a tool position before and after an impact.

12. The tool of claim 1, wherein the linear force is imparted to a surgical site as a condition of an amount of force applied upon the tool by an operator or a surgery robot.

13. A rotary impacting tool for orthopedic surgery, the tool comprising:
    a motor;
    an impact hammer;
    an output anvil;
    a lead screw element; and
    a mechanical spring, wherein the mechanical spring is proximate to the impact hammer for a portion of an operational cycle of the tool, and
    wherein a speed of the motor adjusts to maintain an output RPM during the operational cycle of the tool.

14. The tool of claim 13,
    wherein the impact hammer is disposed on the lead screw element and is rotated by the motor, and wherein the impact hammer is in contact with the output anvil to cause the output anvil to rotate selectively, wherein upon the output anvil ceasing rotation, the impact hammer translates along the lead screw element to energize the mechanical spring, and
    wherein after the impact hammer has translated a sufficient distance away from the output anvil, the mechanical spring imparts its energy on the impact hammer causing the hammer to accelerate along the lead screw element and rotationally impact the output anvil.

15. The tool of claim 13, wherein the impact hammer is energized by the mechanical spring when a torque exceeds a threshold.

16. The tool of claim 13, where a linear impact is limited to a stroke of less than two millimeters per impact.

17. The tool of claim 13, wherein a transition between impacting and non-impacting includes an audible signal.

18. The tool of claim 11, further comprising:
    a sensor, wherein the sensor identifies a forward progress based on a change of one or more of rotary displacement or linear displacement,
    wherein, in response to the sensor identifying that the forward progress is less than a predetermined distance or rotation within a predetermined number of impacts, the tool shuts off, slows down, emits light, or otherwise provides a cue.

19. The tool of claim 13, further comprising:
    a sensor, wherein the sensor determines a tool position before and after an impact.

20. The tool of claim 13, wherein the linear force is imparted to a surgical site as a condition of an amount of force applied upon the tool by an operator or a surgery robot.

* * * * *